United States Patent [19]
Harreus et al.

[11] Patent Number: 6,031,106
[45] Date of Patent: *Feb. 29, 2000

[54] PROCESS AND INTERMEDIATE PRODUCTS FOR PREPARING PYRIDYL-4-FLUOROANILINES

[75] Inventors: Albrecht Harreus, Ludwigshafen; Norbert Götz, Worms; Michael Rack, Heidelberg; Heinz Isak, Böhl-Iggelheim; Peter Schäfer, Ottersheim, all of Germany

[73] Assignee: BASF Aktiengesellschaft, Ludwigshafen, Germany

[ * ] Notice: This patent is subject to a terminal disclaimer.

[21] Appl. No.: 09/142,767
[22] PCT Filed: Mar. 17, 1997
[86] PCT No.: PCT/EP97/01336
  § 371 Date: Sep. 14, 1998
  § 102(e) Date: Sep. 14, 1998
[87] PCT Pub. No.: WO97/34872
  PCT Pub. Date: Sep. 25, 1997

[30] Foreign Application Priority Data

Mar. 18, 1996 [DE] Germany .......................... 196 10 571

[51] Int. Cl.[7] ..................... C07D 213/38; C07D 213/42; C07D 213/61
[52] U.S. Cl. .......................... 546/334; 546/144; 546/173; 546/329
[58] Field of Search ..................... 546/334, 329, 546/144, 173; 504/244

[56] References Cited

U.S. PATENT DOCUMENTS

| | | | |
|---|---|---|---|
| 2,884,458 | 4/1959 | Fidler | 260/580 |
| 3,558,707 | 1/1971 | Churchill et al. | 260/580 |
| 3,580,951 | 5/1971 | Churchill et al. | 260/580 |
| 3,694,509 | 9/1972 | Rylander et al. | 260/578 |
| 3,927,101 | 12/1975 | Leludec | 260/580 |
| 3,992,395 | 11/1976 | Leludec | 260/307 |
| 4,391,991 | 7/1983 | Mundhenke et al. | 564/412 |
| 5,166,401 | 11/1992 | Dugger | 560/43 |
| 5,783,522 | 7/1998 | Schaefer et al. | 504/294 |
| 5,831,093 | 11/1998 | Gotz | 544/335 |

FOREIGN PATENT DOCUMENTS

| | | |
|---|---|---|
| 085890 | 8/1983 | European Pat. Off. |
| 086363 | 8/1983 | European Pat. Off. |
| 147879 | 7/1985 | European Pat. Off. |
| 212375 | 3/1987 | European Pat. Off. |
| 1388523 | 3/1975 | United Kingdom |
| 1428226 | 3/1976 | United Kingdom |
| 2241952 | 9/1991 | United Kingdom |
| 91/17138 | 11/1991 | WIPO |
| 95/02580 | 1/1995 | WIPO |

OTHER PUBLICATIONS

Titov et al., *Obshch. Khim*, 23, 346, 1953.
Patrick et al. *J. Org. Chem.*, 39, 1974, pp. 1758–61.
Tordeaux et al., *J. of Fluorine Chem*, 74, 1995, pp. 251–254.
Houben–Weyl "Methoden der Org. Chemie", vol. 10/1, pp. 1155–1157; vol. E 16a, Part 1, pp. 49–53.

*Primary Examiner*—Evelyn Mei Huang
*Attorney, Agent, or Firm*—Keil & Weinkauf

[57] ABSTRACT

A process for preparing pyridyl-substituted N-phenylhydroxylamines by catalytic hydrogenation of the corresponding nitro compounds in the presence of an N-substituted morpholine compound and rearrangement of the hydroxylamine compounds obtained to pyridyl-4-fluoraniline compounds is described.

20 Claims, No Drawings

PROCESS AND INTERMEDIATE PRODUCTS FOR PREPARING PYRIDYL-4-FLUOROANILINES

This application is the national phase of PCT/EP97/01336, filed Mar. 17, 1997.

The present invention relates to N-phenylhydroxylamine compounds, a process for preparing these compounds and a process for converting these compounds into pyridyl-4-fluoraniline compounds.

2-Pyridyl-4-fluoraniline compounds are described in WO-A-95/02580. They correspond to the formula I

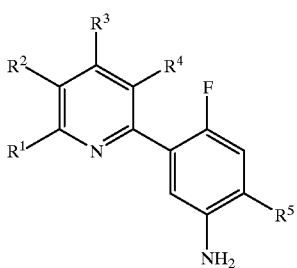

(I)

and are suitable as herbicides for defoliation and desiccation. In addition, they are utilizable as intermediates for preparing phenylpyridines, which are likewise described in WO-A-95/02580. These compounds are synthesized by reaction of a halopyridine of the formula V with a boronic acid of the formula VI in the presence of a transition metal catalyst according to the following reaction scheme:

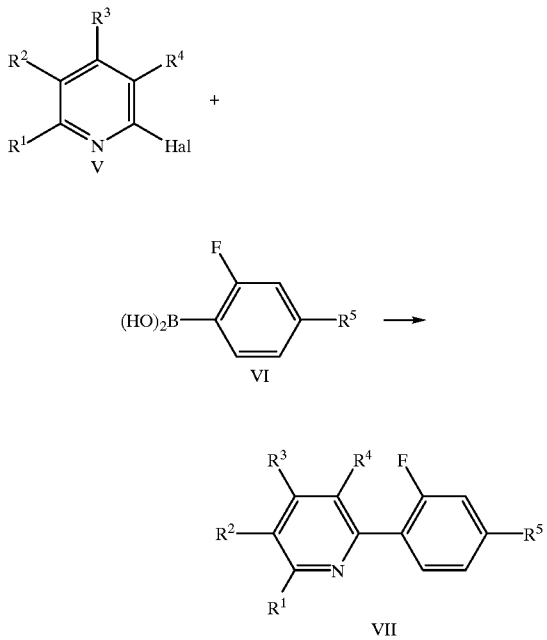

The compounds of the formula I can then be obtained by nitration of a compound of the formula VII to give a compound of the formula VIII and subsequent reduction according to the following reaction scheme:

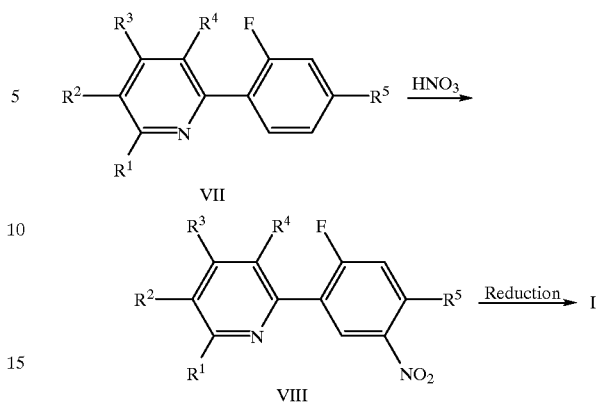

The boronic acid VI is prepared by reaction of the corresponding aryllithium or arylmagnesium compounds with trialkyl borates and subsequent hydrolysis.

This synthesis route, however, is disadvantageous for the following reasons:

In the first stage of the synthesis, fluorine-containing starting compounds are used. These are generally not easily accessible, but have to be prepared via a separate, in some cases multi-stage synthesis. Moreover, the halogen-containing compounds are expensive.

As generally no chemical reaction proceeds quantitatively, in the course of the synthesis halogen-containing and in particular fluorine-containing waste substances are formed, whose disposal can be problematic.

Furthermore, fluorine atoms on aromatic ring systems can be nucleophilically substituted. This demands that in all synthesis stages those reaction components and reaction conditions must be avoided which could lead to a nucleophilic substitution. In addition, reduction conditions are to be avoided, because in this case a defluorination can occur.

If fluorine atoms are substituted on the aromatic system under aqueous conditions, highly corrosive hydrofluoric acid is formed, so that the reactions have to be carried out in expensive special apparatuses.

Finally, the preparation of the arylithium or arylmagnesium compounds mentioned has to be carried out at low temperatures, because otherwise the elimination of metal fluoride with aryne formation appears to interfere or is even the main reaction.

One possibility for preparing 4-fluoroaniline compounds is the introduction of the fluorine atom into the aromatic nucleus by the HF variant of the Bamberger reaction. This variant was until now used especially for the preparation of simple compounds, such as p-fluoroaniline, see Titov et al., Zh. Obshch. Khim 23, 346 (1953), U.S. Pat. No. 4,391,991, WO-A-91/17138 and U.S. Pat. No. 5,166,401. Moreover, Patrick et al. reported in J. Org. Chem. 39, (1974) pages 1759 to 1761 on investigations into substituted N-phenylhydroxy-lamines. In no example were their yields over 61%. It is pointed out here that the range of application of the Bamberger reaction mentioned is generally restricted by the poor availability of the N-phenylhydroxylamine compounds needed. The reason for this is that presently there are no reduction methods which can be generally employed for converting nitroaromatics to the N-phenylhydroxylamines in high yield. In their reductions with zinc dust/ammonium chloride, ammonium sulfide or sodium borohydride, Patrick et al. obtained the desired N-phenylhydroxylamines in at best moderate yields.

In order to get around the disadvantage of the poor accessibility of the N-phenylhydroxylamines, a number of reactions have been described in which the reduction of the nitro compounds was performed in the presence of hydrogen fluoride in order to combine both stages, namely reduction and Bamberger rearrangement, in one stage (U.S. Pat. No. 2,884,458; U.S. Pat. No. 3,580,951; U.S. Pat. No. 3,558,707; DE-A-19 45 625 and GB-A-2,241,952). From this, however, mixtures of the desired p-fluoroaniline and the nonfluorinated aniline which is formed by direct reduction of the nitro compound generally result, see, for example, J. Fluorine Chem. 74 (1995) 251–254. The separation of these chemically very similar compounds, however, is very laborious and associated with high yield losses, see, for example DE-A-1,945,625.

One method for preparing N-phenylhydroxylamines is the long-known catalytic hydrogenation of aromatic nitro compounds (Houben-Weyl "Methoden der Org. Chemie" [Methods of Org. Chemistry], Vol. 10/1 pp. 1155–1157; Vol. E 16a, Part 1, pp. 49–53). In comparison to the relatively expensive electrochemical reduction and to the reduction with metals, such as, for example, with zinc dust, amalgams, etc., which have an unfavorable waste substance balance, catalytic hydrogenation is the most favorable method from the economic point of view. A problem in this type of reaction is further reaction to give the aromatic amine, the stable final product, and the disproportionation of the N-phenylhydroxylamine formed to the corresponding nitroso compounds and anilines. From these undesired intermediates and secondary products, by subsequent reactions, higher molecular weight by-products can be formed, such as azoxybenzenes, azobenzenes, and hydrazobenzenes, which can result, for example, from condensation of nitrobenzenes and N-phenylhydroxylamines and further reaction of the azoxybenzenes formed and under certain circumstances can cause significant yield losses.

Generally, Pd or Pt catalysts are recommended for these hydrogenation reactions. In order to achieve yields or selectivities of >50%, according to the present state of knowledge additions of catalysts in the form of dimethyl sulfoxide, divalent sulfur compounds or various organic phosphorus compounds are necessary (EP-A-85890, EP-A-86363, EP-A-147879, U.S. Pat. No. 3,694,509, EP-A-212375).

With these additives, the improvement in the selectivity is achieved by reduction of the reaction rate, which in turn leads to long reaction times. Furthermore, the partial poisoning or inactivation of the catalyst by the additives has the result that the catalyst has usually lost its activity even after one cycle and has to be renewed.

A further method for preparing phenylhydroxylamines is the catalytic hydrogenation of nitroaromatics in the presence of organic nitrogen bases, such as piperidine, pyrrolidine, pyridine, etc., which, relative to the starting material, have to be employed in an excess (DE-A-2 455 238, DE-OS 2 455 887, DE-A-2 357 370, DE-A-2 327 412). After appropriate working up and purification, the yields achievable by this process are 80–85%. The disadvantage is that with this variant only relatively simple alkyl- and chloronitrobenzenes can be hydrogenated to the corresponding phenylhydroxylamines. Apart from a compound having a 1,3,4-oxadiazole substituent, the hydrogenation of complicated systems by this method is not described.

It is an object of the present invention to make available a process for preparing pyridyl-substituted N-phenylhydroxylamine compounds and for the rearrangement of these compounds to pyridyl-4-fluoroaniline compounds, which process is simple to carry out and gives the desired compounds in high yield and purity.

We have found that this object is achieved if the reduction of the corresponding nitro compounds is carried out by hydrogenation with a platinum or palladium catalyst in the presence of a morpholine compound substituted on the nitrogen atom.

The present invention therefore relates to a process for preparing compounds of the formula II

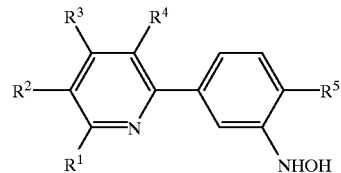

II where $R^1$, $R^3$ and $R^4$, which can be identical or different, are hydrogen, halogen, alkyl, haloalkyl, alkoxyalkyl, alkoxy, alkoxy-alkoxy, hydroxyl, haloalkoxy, alkylcarbonyloxy, haloalkylcarbonyloxy, alkylsulfonyl, haloalkylsulfonyl, $CO_2H$, alkoxycarbonyl, alkoxyalkoxycarbonyl, haloalkoxycarbonyl, alkylcarbonyl, haloalkylcarbonyl, alkoxyalkylcarbonyl, $CONH_2$, alkylaminocarbonyl, dialkylaminocarbonyl, pyrrolidinylcarbonyl, piperidinylcarbonyl, morpholinylcarbonyl, amino, alkylamino, dialkylamino, pyrrolidinyl, piperidinyl, morpholinyl, alkylcarbonylamino, haloalkylcarbonylamino or alkylsulfonylamino;

$R^2$ is halogen, alkyl, haloalkyl, alkoxy or haloalkoxy; or $R^1$ and $R^2$ or $R^2$ and $R^3$ together form a trimethylene or tetramethylene chain; and $R^5$ is halogen, hydroxyl, trifluoromethyl, alkyl or alkoxy, the process comprising hydrogenating a compound of the general formula III

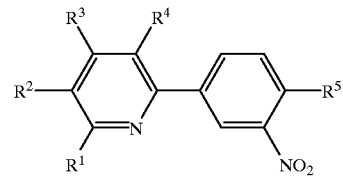

III where $R^1$ to $R^5$ have the meanings indicated above, in the presence of a platinum catalyst or of a sulfur- or selenium-doped palladium catalyst and in the presence of a morpholine compound of the general formula IV

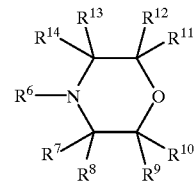

IV where $R^6$ is alkyl and $R^7$ to $R^{14}$, which can be identical or different, are a hydrogen atom or an alkyl radical.

The invention further relates to the hydroxylamine compounds of the formula II, where $R^1$ to $R^5$ have the meanings indicated. Finally, the invention relates to a process for preparing the compounds of the formula I

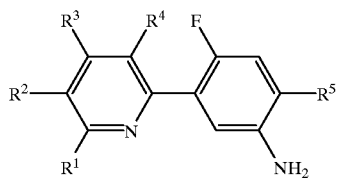

where $R^1$ to $R^5$ have the meanings indicated above, which comprises treating a compound of the formula II with hydrogen fluoride.

In the context of the present invention, alkyl (also in combination with other atoms, groups or substituents, such as alkoxy, haloalkyl, alkylcarbonyloxy, alkylamino, etc.) represents straight-chain or branched alkyl groups which preferably have 1 to 6 carbon atoms, in particular 1 to 5 carbon atoms and particularly preferably 1 to 4 carbon atoms. Examples of alkyl groups are methyl, ethyl, n-propyl, isopropyl, n-butyl, isobutyl, secbutyl, n-butyl, pentyl and isopentyl.

A haloalkyl group can have one or more, in particular 1 to 3 halogen atoms on one or more carbon atoms. The trifluoromethyl group is particularly preferred.

Halogen is fluorine, chlorine or bromine and in particular fluorine or chlorine.

It is surprising and was unforeseeable that the partial hydrogenation of aromatic nitro compounds to the corresponding hydroxylamine derivatives only results in optimum yields and selectivities in the presence of N-alkylmorpholines (N-substituted tetrahydro-1,4-oxazines), which can also be used as solvents, while according to DE-A 24 55 238 organic nitrogen bases, such as pyrrolidines, piperidines, anilines or pyridines, are recommended as the best solvents for this hydrogenation.

As the hydroxylamine derivatives formed as reaction products are very labile compounds which can only be purified with difficulty and decompose relatively rapidly at>100° C., it is all the more important that they are obtained in high yield by the process according to the invention with substantially quantitative conversion, so that laborious purification by removal of starting material and by-products, such as the corresponding anilines, azoxybenzenes, etc. is not necessary.

The preparation of the nitroaromatics needed as starting materials is described in WO-A-95/02580.

The catalysts employed according to the process of the invention contain platinum or palladium, preferably on a carbon support. hen using a palladium catalyst, this must be doped with sulfur or selenium in order to obtain sufficient selectivity. On use in the process according to the invention, platinum yields excellent results even without additional doping. The catalysts can be filtered off after a reaction cycle and used again in the subsequent batch without noticeable loss of activity. In other processes which operate with additives such as dimethyl sulfoxide, dimethylaminopyridine or org. phosphorus compounds (EP-A-86363, EP-A-85890, EP-A-147879), there is generally a rapid decrease in activity due to poisoning of the catalysts.

The platinum or palladium content of the catalyst is not critical and can be varied within wide limits. An expedient content is one of from 0.1 to 15% by weight, preferably from 0.5 to 10% by weight, based on the support material carbon. The amount of the platinum or palladium employed is from 0.001 to 1% by weight, preferably 0.01 to 0.1% by weight, based on the nitro compound. In the preferred embodiment of batchwise hydrogenation, the catalyst is employed as a powder. The presence of the morpholine compounds is of crucial importance for the achievement of very good yields, as these affect the activity of the catalysts in such a way that a high selectivity is achieved in the hydrogenation of nitro compounds to the hydroxylamine derivatives. Preferred morpholine compounds are, for example, 4-methylmorpholine, 4-ethylmorpholine, 4-propylmorpholine, 4-n-butylmorpholine, 4-isobutylmorpholine, 4-tertiary-butylmorpholine, 4-n-pentylmorpholine, 4-isopentylmorpholine 2,4,6-trimethylmorpholine 2,3,4,5,6-pentamethylmorpholine and 2,2,4,6,6-pentamethylmorpholine.

Generally, the morpholine is employed in an excess, i.e. the weight ratio of morpholine to the nitro compound is greater than 1.

The temperature for the partial hydrogenation is generally in the range from −20° C. to +100° C., preferably −5 to +50° C. In order to avoid overhydrogenation, at the temperature at which the hydrogenation proceeds sufficiently rapidly a pressure is set which is between normal pressure and 10 bar overpressure. Normally, the hydrogen is introduced into the hydrogenation reactor as a gas at normal pressure or slightly elevated pressure. Preferably, the hydrogenation is carried out without further solvents or diluents, such as, for example, alcohols or ethers.

The hydroxylamine compounds obtained are rearranged to the desired pyridyl-4-fluoraniline compounds by treatment with anhydrous hydrogen fluoride. The reaction component is used here in amounts such that the molar ratio of hydrogen fluoride to compound of the formula II is preferably in the range from 10 to 50 and in particular in the range from 20 to 30.

The following measures have proven to be particularly preferable for carrying out the rearrangement:

a) The desired amount of hydrogen fluoride is initially introduced and the hydroxylamine is slowly added. Preferably, the hydroxylamine is introduced as a solid. If the reaction components are brought into contact in the reverse sequence, the product is obtained in poorer yield and lower purity.

b) The hydroxylamine is added in the range from −70 to 0° C., in particular −40 to −20° C. After addition is complete, the temperature is allowed to rise, if desired utilizing the intrinsic heat of reaction, until reflux conditions are present.

c) Atmospheric oxygen is excluded by working under inert gas, such as nitrogen or argon.

d) The reaction is carried out without organic solvents.

The reaction time depends on the reaction temperature and the starting materials. In general, it is from 5 to 24 hours.

After reaction is complete, working up is carried out in a customary manner. It has proved expedient to drive off the hydrogen fluoride to the greatest extent possible by means of heating and passage of nitrogen. The residue is then taken up in an inert organic solvent, for example a chlorinated solvent such as dichloromethane or an ether such as diethyl ether. Water is added and the mixture is rendered alkaline in order to liberate the amine base, which is then extracted using a suitable inert solvent, such as diethyl ether or dichloromethane. If necessary, purification can be carried out by means of customary methods, such as recristallization and chromatography.

The following examples illustrate the invention without restricting it.

EXAMPLE 1

N-2-Chloro-5-(3-chloro-5-trifluoromethyl-2-pyridyl)phenylhydroxylamine

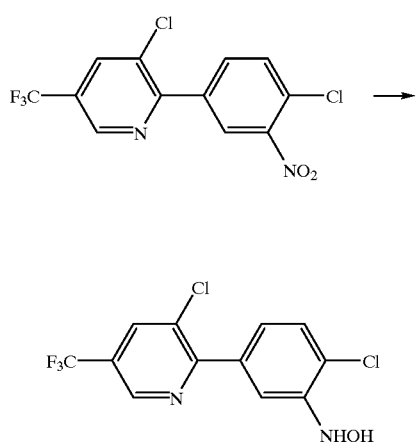

A solution of 108 g (0.324 mol) of 2-chloro-5-(3-chloro-5-trifluoromethyl-2-pyridyl)nitrobenzene in 1.1 l of N-methyl-morpholine and 4 g of 5% strength by weight platinum on carbon (Type F 103 RS/W from Degussa) were added to a 2 l hydrogenation apparatus. After inertizing with nitrogen, hydrogen was passed in with vigorous stirring at 25–30° C. and a hydrogen overpressure of 0.1 bar until absorption no longer took place (about 6 h and consumption of 14.8 l of hydrogen).

The material removed from the reaction was filtered through animal charcoal and the filtrate was evaporated under reduced pressure at a bath temperature of at most 60° C. 100 g of high-boiling gasoline (180–210° C.) were added to the remaining residue and the gasoline/N-methylmorpholine mixture was fractionally distilled with the aid of a Vigreux column (b.p. 28–30° C. at 0.5 mbar). The crystals deposited in the distillation bottom were filtered off with suction, washed with n-hexane and dried.

103 g of the title compound were obtained (corresponds to a yield of 98%). M.p.: 103–105° C. (dec.)

250 MHz $^1$H-NMR (DMSO-d$_6$, ε in ppm) 9.05 (s, 1H), 8.7 (s, 1H), 8.55 (d, 1H); 8.5 (s, 1H); 7.57 (d, 1H); 7.41 (d, 1H); 7.15 (d, 1H)

Prepared in a similar manner: N-5-(3-Chloro-5-trifluoromethyl-2-pyridyl)-2-methoxyphenylhydroxylamine

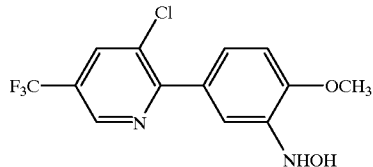

200 MHz $^1$H-NMR (DMSO-d$_6$, ε in ppm) 9.0 (s, 1H); 8.5 (broad s, 1H), 7.95 (broad s, 1H); 7.5 (s, 1H); 7.25 (d, 1H); 7.0 (d, 1H); 3.8 (s, 3H)

EXAMPLE 2

2-Chloro-4-fluoro-5-(3-chloro-5-trifluoromethyl-2-pyridyl)-4-fluoraniline

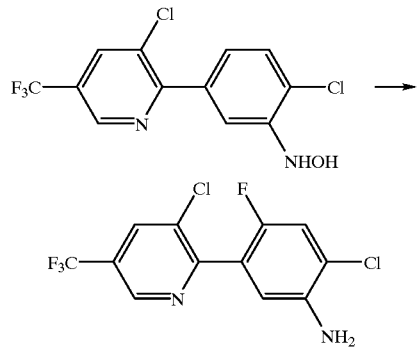

A 1 l Teflon reaction vessel (equipped with reflux condenser, gas-inlet tube, internal temperature measurement) was cooled, after inertizing with nitrogen, in a dry-ice bath and the cooling circulation in the reflux condenser was adjusted to −15° C. The condensing-in of the hydrogen fluoride was begun, the internal temperature in the course of this being in the range from −49 to −66° C. After a total of 317 g (15.9 mol) of hydrogen fluoride had been introduced, the HF gas-inlet tube was removed and 162 g (0.5 mol) of N-2-chloro-5-(3-chloro-5-trifluoromethyl-2-pyridyl)phenylhydroxylamine (Example 1) was introduced in portions in the course of 30 min. During the course of this the internal temperature rose to −48° C. The cooling bath was then removed, the temperature of the cooling circulation in the waste gas condenser was raised to 25° C. and the reaction mixture was allowed to come to ambient temperature. After 3 hours it had reached 23° C. In the following 2 hours the internal temperature increased to a maximum of 36° C.

10 hours after metering-in was complete, the temperature in the cooling circulation was increased to 30° C. and the escaping hydrogen fluoride gas was passed into a scrubber containing potassium hydroxide solution. Later, the reaction vessel was additionally flushed with nitrogen.

After this the reaction vessel was opened and the dark, liquid reaction mixture was introduced in portions into 400 g of ice with vigorous stirring. The vessel was rinsed with a total of 300 ml of dichloromethane. The two-phase mixture was then adjusted to pH=10 using 25% strength ammonia solution. After separating off the organic phase, the aqueous phase was extracted twice more with 350 ml of dichloromethane each time, the organic phases were combined and dried over magnesium sulfate and the solvent was finally evaporated under reduced pressure.

155 g of a solid residue were obtained, which was recrystallised from 780 ml of n-hexane, cooling in an ice-bath. Yield: 140.2 g (86% of theory) of the title compound. Purity according to GC:> 99 area %. M.p.: 94–95° C.

270 MHz $^1$H-NMR (CDCl$_3$, ε in ppm) 8.85 (s, 1H); 8.05 (s, 2H), 7.15 (d, 1H); 6.81 (d, 1H); 4.5 (s, 2H)

We claim:

1. An N-phenylhydroxylamine compound of the formula II

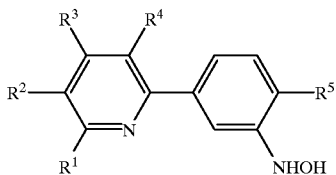

where $R^1$, $R^3$ and $R^4$, which are identical or different, are hydrogen, halogen, alkyl, haloalkyl, alkoxyalkyl, alkoxy, alkoxyalkoxy, hydroxyl, haloalkoxy, alkylcarbonyloxy, haloalkylcarbonyloxy, alkylsulfonyl, haloalkylsulfonyl, $CO_2H$, alkoxycarbonyl, alkoxyalkoxycarbonyl, haloalkoxycarbonyl, alkylcarbonyl, haloalkylcarbonyl, alkoxyalkylcarbonyl, $CONH_2$, alkylaminocarbonyl, dialkylaminocarbonyl, pyrrolidinylcarbonyl, piperidinylcarbonyl, morpholinylcarbonyl, amino, alkylamino, dialkylamino, pyrrolidinyl, piperidinyl, morpholinyl, alkylcarbonylamino, haloalkylcarbonylamino or alkylsulfonylamino;

$R^2$ is halogen, alkyl, haloalkyl, alkoxy or haloalkoxy; or $R^1$ and $R^2$ or $R^2$ and $R^3$ together form a trimethylene or tetramethylene chain; and $R^5$ is halogen, hydroxyl, trifluoromethyl, alkyl or alkoxy.

2. A compound, of the formula II as defined in claim 1, where $R^1$, $R^3$ and $R^4$, which are identical or different, are hydrogen, halogen, alkyl, haloalkyl, alkoxy, hydroxyl, haloalkoxy or alkylsulfonyl.

3. A compound, of the formula II as defined in claim 1, where $R^1$, $R^3$ and $R^4$, which are identical or different, are hydrogen, halogen, alkyl or haloalkyl.

4. A compound, of the formula II as defined in claim 1, where $R^2$ is halogen or haloalkyl.

5. A compound, of the formula II as defined in claim 1, where $R^5$ is hydrogen, halogen or alkoxy.

6. A compound, of the formula II as defined in claim 1, where $R^1$ and $R^3$ are hydrogen, $R^2$ is halogen or haloalkyl; $R^4$ is alkyl or halogen; and $R^5$ is hydrogen, halogen or alkoxy.

7. A process for preparing a compound of the formula II as claimed in claim 1, which comprises hydrogenating a compound of the formula III

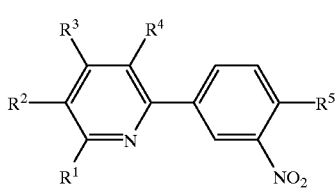

where $R^1$ to $R^5$ have the meanings indicated in claim 1, in the presence of a platinum catalyst or of a sulfur- or selenium-doped palladium catalyst and in the presence of a morpholine compound of the formula IV

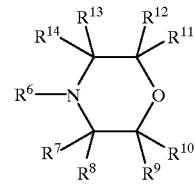

where $R^6$ is alkyl and $R^7$ to $R^{14}$, which are identical or different, are a hydrogen atom or an alkyl radical.

8. A process as defined in claim 7, wherein, as morpholine compound of the formula IV, 4-methylmorpholine, 4-ethylmorpholine, 4-propylmorpholine, 4-n-butylmorpholine, 4-isobutylmorpholine, 4-t-butylmorpholine, 4-n-pentylmorpholine, 4-isopentylmorpholine, 2,4,6-trimethylmorpholine, 2,3,4,5,6-pentamethylmorpholine or 2,2,4,6,6-pentamethylmorpholine is used.

9. A process as defined in claim 7, wherein the weight ratio of morpholine compound of the formula IV to nitro compound of the formula III is greater than 1.

10. A process as defined in claim 7, wherein a catalyst on an active carbon support is used.

11. A process as defined in claim 7, wherein the platinum catalyst or the palladium catalyst is used in an amount from 0.001 to 1.0% by weight of platinum or palladium, based on the nitro compound.

12. A process as defined in claim 7, wherein the hydrogenation is carried out in the range from −20° C. to 100° C.

13. A process as defined in claim 7, wherein the hydrogenation is carried out at a pressure in the range from normal pressure to an overpressure of 10 bars.

14. A process for preparing a compound of the formula I

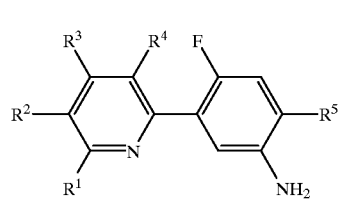

where $R^1$ to $R^5$ have the meanings indicated in claim 1, which comprises treating a compound of the formula II of claim 1 with hydrogen fluoride.

15. A process as claimed in claim 14, wherein the molar ratio of hydrogen fluoride to compound of the formula II is in the range from 10 to 50.

16. A process as defined in claim 14, wherein the hydrogen fluoride is initially introduced and the compound of the formula II is gradually added.

17. A process as defined in claim 16, wherein the compound of the formula II is added in solid form.

18. A process as defined in claim 16, wherein the addition of the compound of the formula II is carried out in the range from −70 to −40° C.

19. A process as defined in claim 18, wherein the temperature is slowly increased after addition of the compound of the formula II is complete.

20. A process as defined in claim 14, wherein a compound of the formula II is prepared by hydrogenating a compound of the formula III

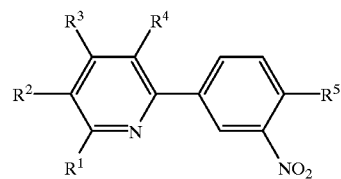
III
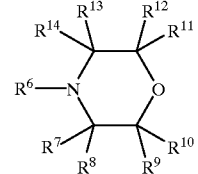
IV
where $R^1$ to $R^5$ have the meanings indicated in claim 1, in the presence of a platinum catalyst or a sulfur- or selenium-doped palladium catalyst and in the presence of a morpholine compound of the formula IV
where $R^6$ is alkyl and $R^7$ to $R^{14}$, which are identical or different, are a hydrogen atom or an alkyl radical.
* * * * *